US010753204B2

(12) United States Patent
Smith

(10) Patent No.: US 10,753,204 B2
(45) Date of Patent: Aug. 25, 2020

(54) SYSTEMS AND METHODS FOR MONITORING AND MANAGING WELLHEAD EMISSIONS

(71) Applicant: Steve Smith, Seabrook, TX (US)

(72) Inventor: Steve Smith, Seabrook, TX (US)

( * ) Notice: Subject to any disclaimer, the term of this patent is extended or adjusted under 35 U.S.C. 154(b) by 234 days.

(21) Appl. No.: 15/796,412

(22) Filed: Oct. 27, 2017

(65) Prior Publication Data

US 2018/0119544 A1  May 3, 2018

Related U.S. Application Data

(60) Provisional application No. 62/413,859, filed on Oct. 27, 2016.

(51) Int. Cl.
*E21B 49/08* (2006.01)
*E21B 47/10* (2012.01)
*G01N 33/00* (2006.01)

(52) U.S. Cl.
CPC ............ *E21B 49/086* (2013.01); *E21B 47/10* (2013.01); *E21B 49/08* (2013.01); *G01N 33/0004* (2013.01); *G01N 33/0075* (2013.01)

(58) Field of Classification Search
CPC ........ E21B 47/10; E21B 49/08; E21B 49/086; G01N 33/0004; G01N 33/0075
See application file for complete search history.

(56) References Cited

U.S. PATENT DOCUMENTS

| 4,925,633 A * | 5/1990 | Doyle | B01D 53/8637 |
| | | | 422/171 |
| 2005/0238549 A1* | 10/2005 | Hammel | C22B 7/006 |
| | | | 422/168 |
| 2007/0137181 A1* | 6/2007 | Upadhyay | F01N 3/0253 |
| | | | 60/286 |

* cited by examiner

*Primary Examiner* — Paul M. West
(74) *Attorney, Agent, or Firm* — Conley Rose, P.C.

(57) ABSTRACT

An emissions monitoring and management system includes a containment assembly that defines an enclosed volume, wherein the enclosed volume of the containment assembly is configured to receive an industrial component, a fluid conduit coupled to the containment assembly and in fluid communication with the enclosed volume, an emissions conditioner coupled to the fluid conduit, wherein the emissions conditioner is configured to reduce a concentration of a predetermined gas of interest in the fluid conduit, a first emissions detector coupled to the containment assembly and in fluid communication with the enclosed volume, wherein the first emissions detector is configured to determine a concentration of the predetermined gas of interest in the enclosed volume, and a transmitter in signal communication with the first emissions detector, wherein the transmitter is configured to transmit signals corresponding to a first predetermined concentration of the predetermined gas of interest in the enclosed volume.

19 Claims, 10 Drawing Sheets

SYSTEMS AND METHODS FOR MONITORING AND MANAGING WELLHEAD EMISSIONS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

This disclosure relates generally to systems and methods for monitoring and managing reactive emissions such as Methane and volatile organic compounds (VOCs). More particularly, this disclosure relates to systems and methods for monitoring and managing reactive emissions emitted from wellheads, artificial lifts or hydrocarbon production equipment Hydrocarbon production systems, both actively producing and abandoned, represent potential leak sources of environmentally hazardous reactive emissions including VOCs, methane, etc. Potential leaks sources in the upstream environment may include wellheads and other equipment utilized for extracting hydrocarbons from subterranean earthen formations. In some jurisdictions, environmental regulations may require the monitoring of potential leak sources of environmentally hazardous reactive emissions in the upstream environment. For instance, some jurisdictions may require periodic testing or active monitoring of potential leak points to ensure that any leakage of reactive emissions to the surrounding environment is identified and subsequently addressed. A periodic testing regimen, due to its relative inflexibility, may result in delays in the identification of a leak, as well as costly repairs and potential legal fines for materials leaked to the surrounding environment prior to the identification and remediation of the leak.

BRIEF SUMMARY OF THE DISCLOSURE

An embodiment of an emissions monitoring and management system comprises a containment assembly that defines an enclosed volume, wherein the enclosed volume of the containment assembly is configured to receive an industrial component, a fluid conduit coupled to the containment assembly and in fluid communication with the enclosed volume, an emissions conditioner coupled to the fluid conduit, wherein the emissions conditioner is configured to reduce a concentration of a predetermined gas of interest in the fluid conduit, a first emissions detector coupled to the containment assembly and in fluid communication with the enclosed volume, wherein the first emissions detector is configured to determine a concentration of the predetermined gas of interest in the enclosed volume, and a transmitter in signal communication with the first emissions detector, wherein the transmitter is configured to transmit signals corresponding to a first predetermined concentration of the predetermined gas of interest in the enclosed volume. In some embodiments, the system further comprises a computer in wireless communication with the transmitter, wherein the computer is configured to output an emissions report including the concentration of the predetermined gas of interest in the enclosed volume. In some embodiments, the system further comprises a second emissions detector coupled to a fluid outlet extending from the emissions conditioner, wherein the second emissions detector is in fluid communication with a surrounding environment, and wherein the second emissions detector is configured to determine a concentration of the predetermined gas of interest in the fluid outlet, wherein the computer is in signal communication with the first and second emissions detectors and is configured to determine an efficiency of the emissions conditioner based on the difference between concentration of the predetermined gas of interest in the enclosed volume determined by the first emissions detector and the concentration of the predetermined gas of interest in the fluid outlet determined by the second emissions detector. In certain embodiments, the system further comprises a pump coupled to the fluid conduit and configured to pump the predetermined gas of interest from the enclosed volume through the fluid conduit to the emissions conditioner. In certain embodiments, the emissions conditioner comprises a scrubber, a catalytic converter, or a tesla converter. In some embodiments, the emissions conditioner is a catalytic converter comprising a temperature switch configured to monitor a temperature of the catalytic converter, and wherein the transmitter is in signal communication with the temperature switch. In some embodiments, the transmitter is configured to transmit signals corresponding to a second predetermined concentration of the predetermined gas of interest in the enclosed volume, wherein the second predetermined concentration is greater than the first predetermined concentration. In certain embodiments, the containment assembly comprises a plurality of flexible panels suspended from a frame, and wherein the enclosed volume is in fluid communication with the surrounding environment. In certain embodiments, the containment assembly comprises a containment vessel sealed from the surrounding environment. In some embodiments, the system further comprises a pressure differential switch coupled to the containment vessel, and a controller in communication with the pressure differential switch, wherein the controller is configured to actuate the pump to maintain a negative pressure in the enclosed volume relative to the surrounding environment. In some embodiments, the industrial component comprises a wellhead. In certain embodiments, the system further comprises a flow switch configured to measure a fluid flow rate in the emissions conditioner, wherein the flow switch is in signal communication with the transmitter.

An embodiment of an emissions monitoring and management system comprises a containment assembly that defines an enclosed volume, wherein the enclosed volume of the containment assembly is configured to receive an industrial component, the containment assembly has a first end, a second end opposite the first end, the containment assembly comprising a plurality of flexible panels extending between the first end and the second end, the panels defining the enclosed volume, wherein the containment assembly comprises a retracted position spaced from the industrial component and an extended position at least partially covering the industrial component when the containment assembly is located over the industrial component, a fluid conduit coupled to the containment assembly and in fluid communication with the enclosed volume, an emissions conditioner coupled to the fluid conduit, wherein the emissions conditioner is configured to reduce a concentration of a predetermined gas of interest in the fluid conduit, a first emissions detector coupled to the containment assembly and in fluid communication with the enclosed volume, wherein the first emissions detector is configured to detect the presence of the predetermined gas of interest in the enclosed volume, and a retraction mechanism coupled to the containment assembly and configured to selectively actuate the containment assembly between the retracted position and the extended position. In some embodiments, the system further comprises a support frame that physically supports the containment assembly, the support frame comprising a plurality of laterally spaced legs defining lateral sides of the support frame, a support beam extending between a pair of the plurality of laterally spaced legs that defines a top of the support frame, wherein the containment assembly further comprises a containment cap attached to a first end of each flexible panel via a bracket assembly, the containment cap comprising a detector port that receives the first emissions detector, a plurality of elongate containment seals that sealingly engage the flexible panels and the bracket assembly to restrict fluid disposed in the enclosed volume from escaping into the surrounding environment at the first end of the containment assembly. In some embodiments, each of the plurality of legs of the support frame comprises a tubular member including an internal cavity configured to receive ballast, and at least one of the plurality of legs of the support frame includes a fill aperture at a first end of the leg and a drain aperture at a second end of the leg opposite the first end, and wherein both the fill aperture and the drain aperture are configured to allow for the selective passage of ballast therethrough. In certain embodiments, the containment assembly further comprises a plurality of elongate ribs extending laterally along the flexible panels, wherein each of the plurality of elongate ribs, legs, and beams comprise a plastic material. In certain embodiments, the system further comprises a second emissions detector coupled to a fluid outlet extending from the emissions conditioner, wherein the second emissions detector is in fluid communication with a surrounding environment, and wherein the second emissions detector is configured to determine a concentration of the predetermined gas of interest in the fluid outlet, a transmitter in signal communication with the first and second emissions detectors, and a computer in signal communication with the first and second emissions detectors, wherein the first emissions detector is configured to determine a concentration of the predetermined gas of interest in the enclosed volume, wherein the transmitter is configured to transmit signals corresponding to a first predetermined concentration of the predetermined gas of interest in the enclosed volume, and wherein the computer is configured to measure an efficiency of the emissions conditioner based on the difference between concentration of the predetermined gas of interest in the enclosed volume determined by the first emissions detector and the concentration of the predetermined gas of interest in the fluid conduit determined by the second emissions detector.

An embodiment of a method for monitoring and managing emissions from an industrial component comprises (a) at least partially covering the industrial component with a containment assembly that defines an enclosed volume, (b) determining a concentration of a predetermined gas of interest in the enclosed volume, (c) communicating one or more gases from the enclosed volume through a fluid conduit to an emissions conditioner to reduce a concentration of the predetermined gas of interest in the fluid conduit, (d) determining a concentration of the predetermined gas of interest in a fluid outlet extending from the emissions conditioner, and (e) transmitting signals corresponding to a first predetermined concentration of the predetermined gas of interest in the enclosed volume. In some embodiments, the method further comprises (f) actuating the containment assembly between a retracted position spaced from the industrial component and an extended position at least partially covering the industrial component. In some embodiments, the method further comprises (f) determining an efficiency of the emissions conditioner based on the difference between concentration of the predetermined gas of interest in the enclosed volume and the concentration of the predetermined gas of interest in the fluid outlet.

BRIEF DESCRIPTION OF THE DRAWINGS

For a detailed description of the disclosed embodiments, reference will now be made to the accompanying drawings in which.

DETAILED DESCRIPTION OF THE DISCLOSED EMBODIMENTS

Figure 1:
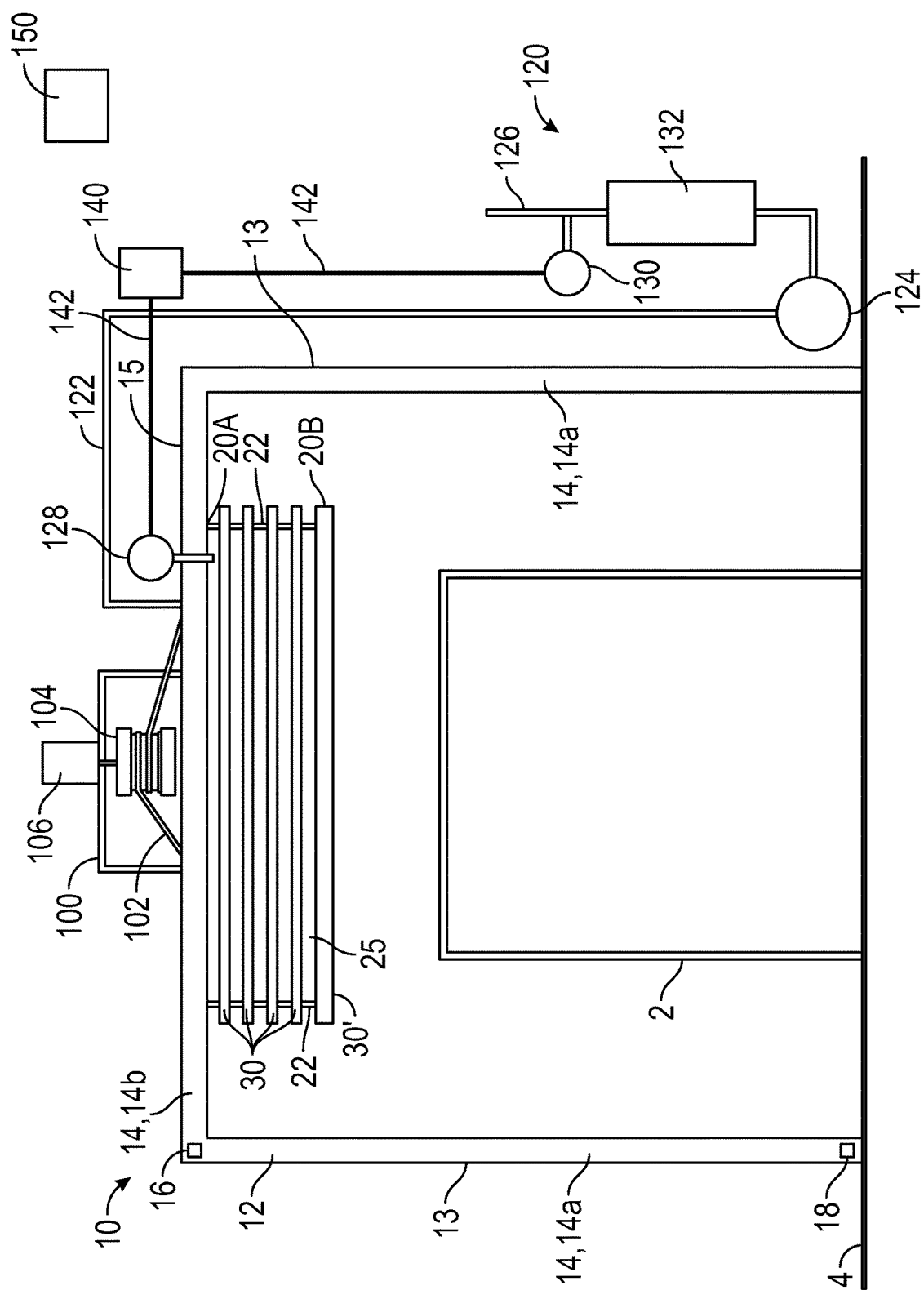
FIG. 1 is a schematic view of an embodiment of an emissions monitoring and management system in a first position in accordance with principles disclosed herein.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 2:
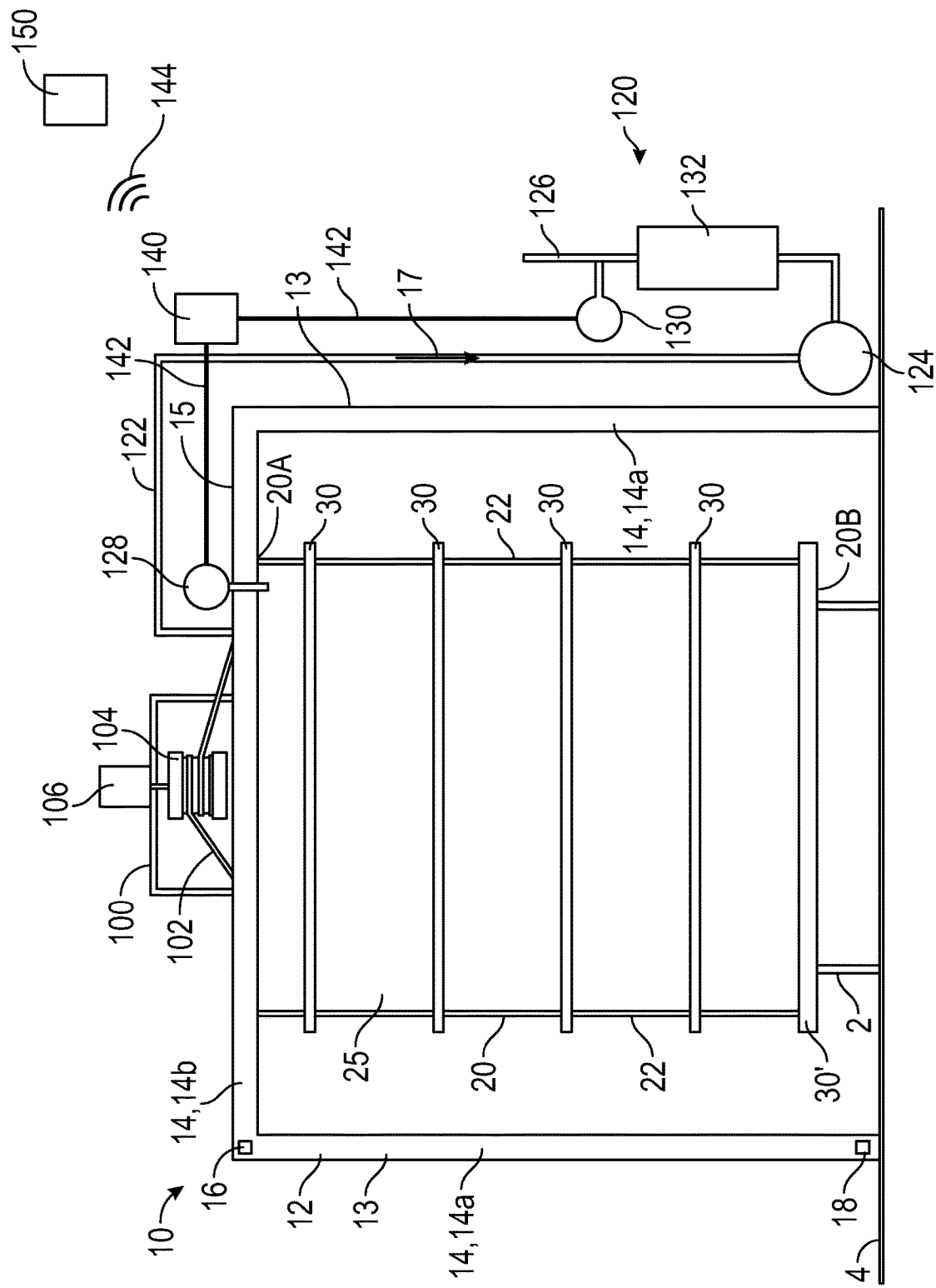
FIG. 2 is a schematic view of the emissions monitoring and management system of FIG. 1 in a second position in accordance with principles disclosed herein.
Figure 3:
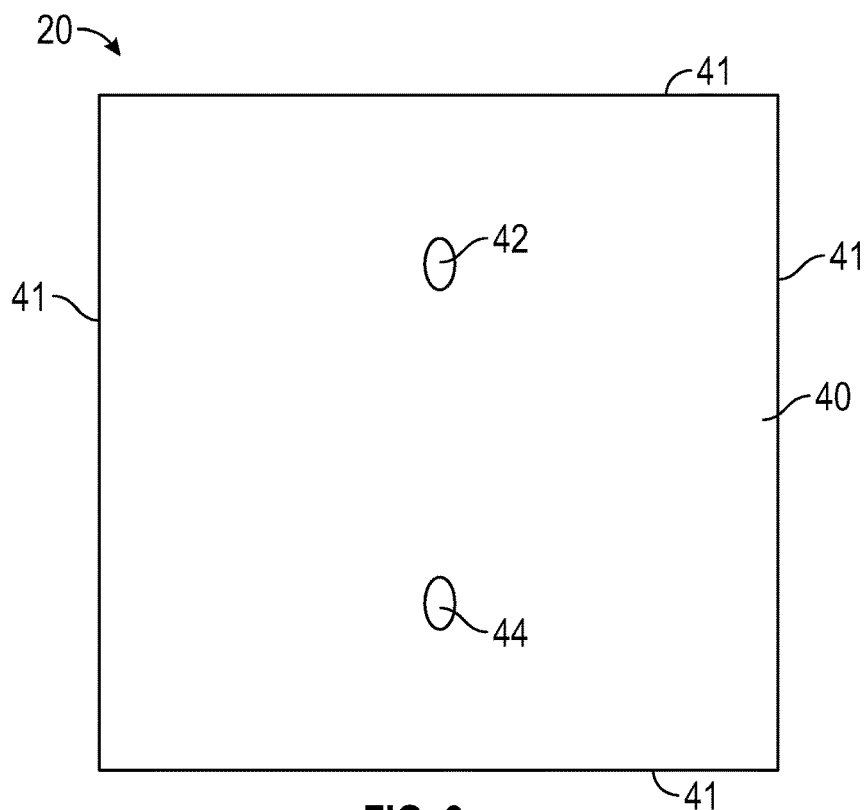
FIG. 3 is a top view of an embodiment of a containment cap of a containment assembly of the emissions monitoring and management system of FIG. 1 in accordance with principles disclosed herein.

Referring now to FIGS. 1, 2, an embodiment of an emissions monitoring and management system 10 is shown. In general, system 10 is configured to detect and mitigate emissions, such as emissions of VOCs or other reactive compounds, from an industrial component. In the embodiment shown in FIGS. 1, 2, system 10 is configured to detect and mitigate emissions from a wellhead 2 disposed in a remote location. In this embodiment, system 10 includes an outer support frame 12, a containment assembly 20 suspended from frame 12, a retraction mechanism 100 coupled to frame 12 and assembly 20, and a detection and mitigation system 120. Support frame 12 is set on the surface 4 of the ground and physically supports containment assembly 20, retraction mechanism 100, and select components of detection and mitigation system 120. In this embodiment, support frame 12 is portable such that system 10 can be deployed, assembled, and installed at a first remote location (e.g., the location of wellhead 2, etc.), and if desired, subsequently disassembled and moved to a second location located at a distance from the first location. In this manner, emissions monitoring and management system 10 may be installed around wellhead 2 for detecting and mitigating emissions therefrom and, later on, removed from wellhead 2 and installed around another industrial component, such as another wellhead disposed distal wellhead 2, for detecting mitigating emissions therefrom.

In this embodiment, support frame 12 is a rectangular prismatic frame 12 including a plurality of rigid interconnected elongate support members 14. In this embodiment, members 14 of frame 12 include four vertically oriented, laterally spaced legs 14a and four horizontally oriented support beams 14b. Legs 14a define the four corners of frame 12 and one beam 14b extends between each pair of adjacent legs 14a. Particularly, the ends of beams 14b are secured to the upper ends of legs 14a. In this arrangement, support frame 12 may be described as having four lateral sides 13 defined by legs 14a, lateral sides 13 extending vertically from surface 4 to beams 14b and a horizontally oriented top 15 defined by support beams 14b.

In this embodiment, support members 14 each comprise a tubular member having an inner cavity in fluid communication with the fluid cavities of the tubular members comprising the other support members 14. The lower ends of legs 14a are closed off such that the interconnected cavities can be filled with ballast (e.g., water, sand, etc.). Although members 14 can be made of any suitable rigid material such as steel or rigid polymer, in this embodiment, support members 14 comprise polyvinyl chloride (PVC) pipes. As such, members 14 are relatively lightweight and can be assembled together and broken down with relative ease.

Referring still to FIGS. 1, 2, at least one first or fill aperture 16 is provided in at least one support member 14 proximal top 15 of support frame 12, and at least one second or drain aperture 18 is provided in at least one support member 14 proximal surface 4. When the internal cavities of support members 14 are filled with ballast, each aperture 16, 18 is closed and sealed with a removal plug. Apertures 16, 18 provide access to the interconnected cavities within members 14 such that frame 12 can be constructed and installed around wellhead 2, and subsequently filled with ballast via fill aperture 16 to increase the weight of support frame 12 and thereby more securely position frame 12 at the desired position around wellhead 2. Once it is desired to remove emissions monitoring and management system 10 from wellhead 2, the plug sealing drain aperture 18 is removed to drain the ballast from the internal cavities of support members 14 of the support frame 12, thereby reducing the weight of frame 12 to aid in disassembly and transport of frame 12.

Referring to FIGS. 1-11, containment assembly 20 of system 10 captures and contains any emissions (e.g., VOCs or other reactive compounds) released from wellhead 2, thereby restricting and/or preventing such emissions from escaping into the environment surrounding containment assembly 20. In addition, containment assembly 20 directs emissions released from wellhead 2 into detection and mitigation system 120 such that the emissions may be treated therein before being released to the surrounding environment.

In the embodiment shown in FIGS. 1-11, containment assembly 20 has a first or upper end 20A distal surface 4 and a second or lower end 20B opposite upper end 20A and positionable proximal surface 4. In addition, containment assembly 20 includes a plurality of vertically oriented flexible curtains or panels 22 (shown as 22A-22E in FIGS. 4-10), a plurality of elongate horizontally oriented support ribs 30 extending laterally along panels 22 (shown in FIGS. 1, 2), a containment cap 40 attached to the upper ends of panels 22 and positioned at the upper end 20A of containment assembly 20, a plurality of elongate containment seals 50 (shown in FIGS. 9, 10) sealingly engaging curtain panels 22 and a containment bracket assembly 60 disposed about laterally extending sides 41 (shown in FIG. 10) of containment cap 40. As will be described in more detail below, retraction mechanism 100 can be operated to raise and lower panels 22 relative to the surface 4, thereby raising and lowering the lower end 20B of containment assembly 20 relative to the surface 4. Thus, containment assembly 20 and panels 22 may be described as having a first or retracted position (FIG. 1) with lower end 20B vertically raised and positioned proximal upper end 20A and distal surface 4, and a second or extended position (FIG. 2) with lower end 20B vertically lowered and positioned distal upper end 20A. It should be appreciated that in the extended position, lower end 20B is proximal to but vertically spaced above the ground 4.

Figure 4:
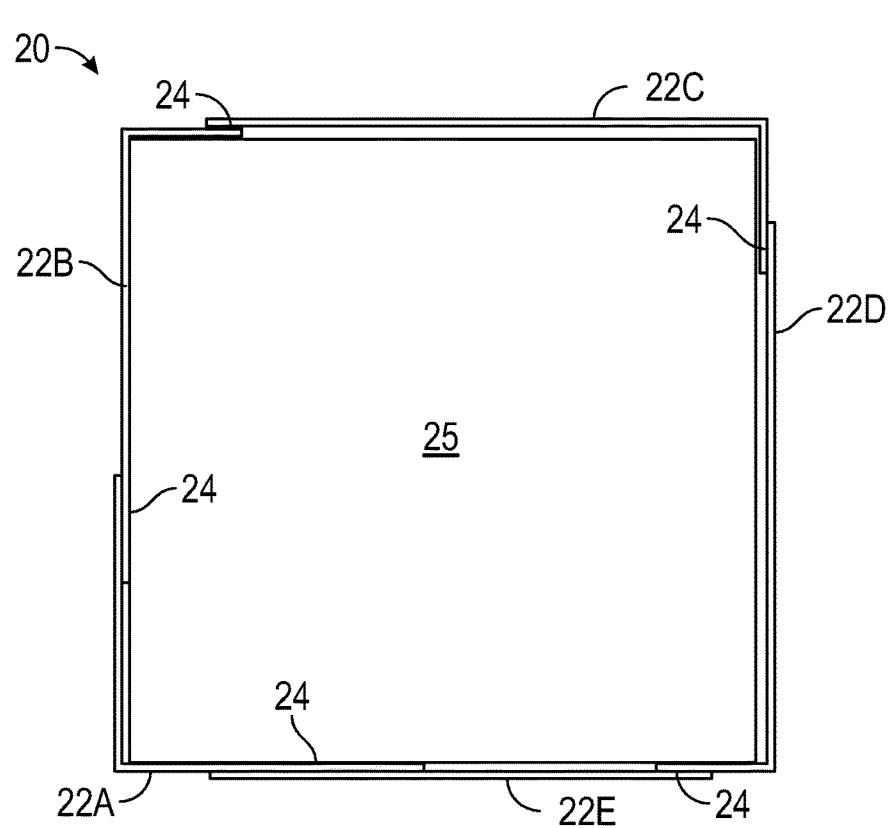
FIG. 4 is a top view of an embodiment of a containment assembly of the emissions monitoring and management system of FIG. 1 in accordance with principles disclosed herein.
Figure 6:
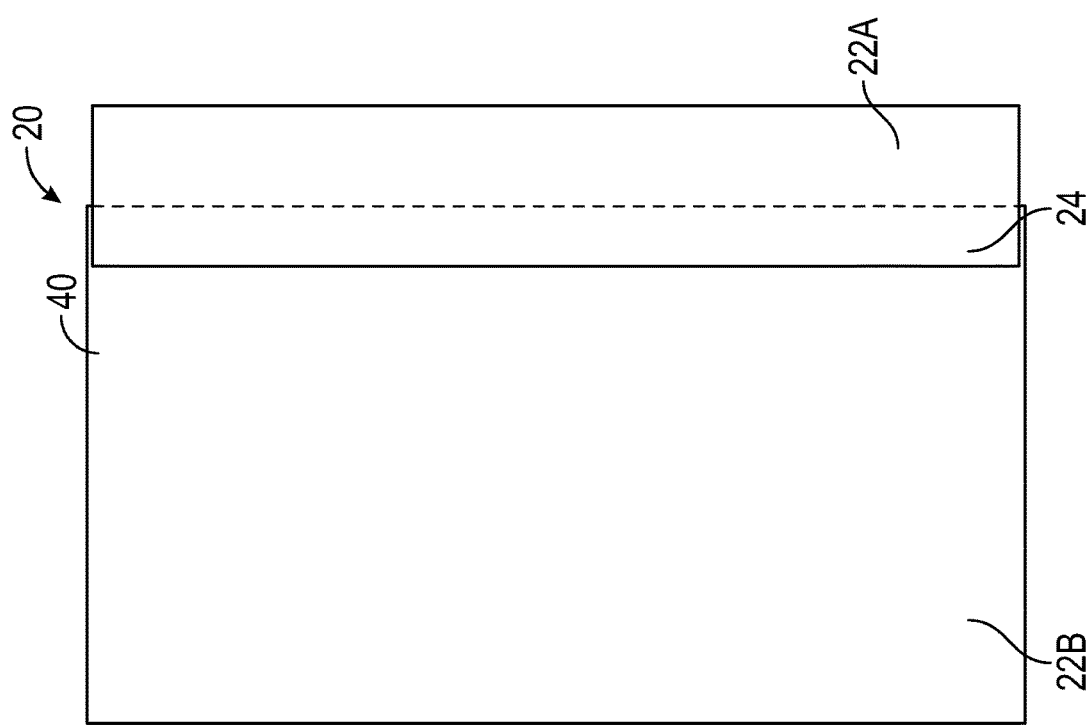
FIG. 6 is a second side view of the containment assembly of FIG. 4.
Figure 5:
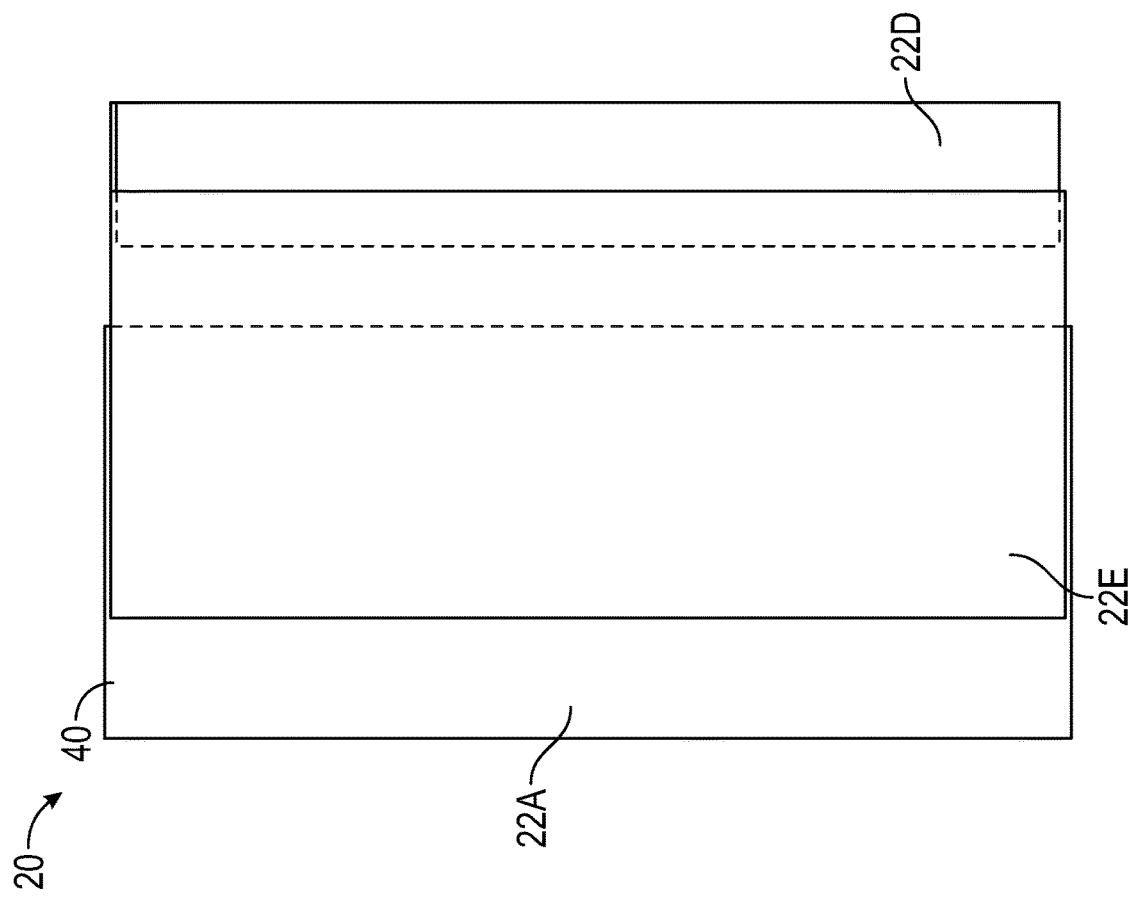
FIG. 5 is a first side view of the containment assembly of FIG. 4.
Figure 8:
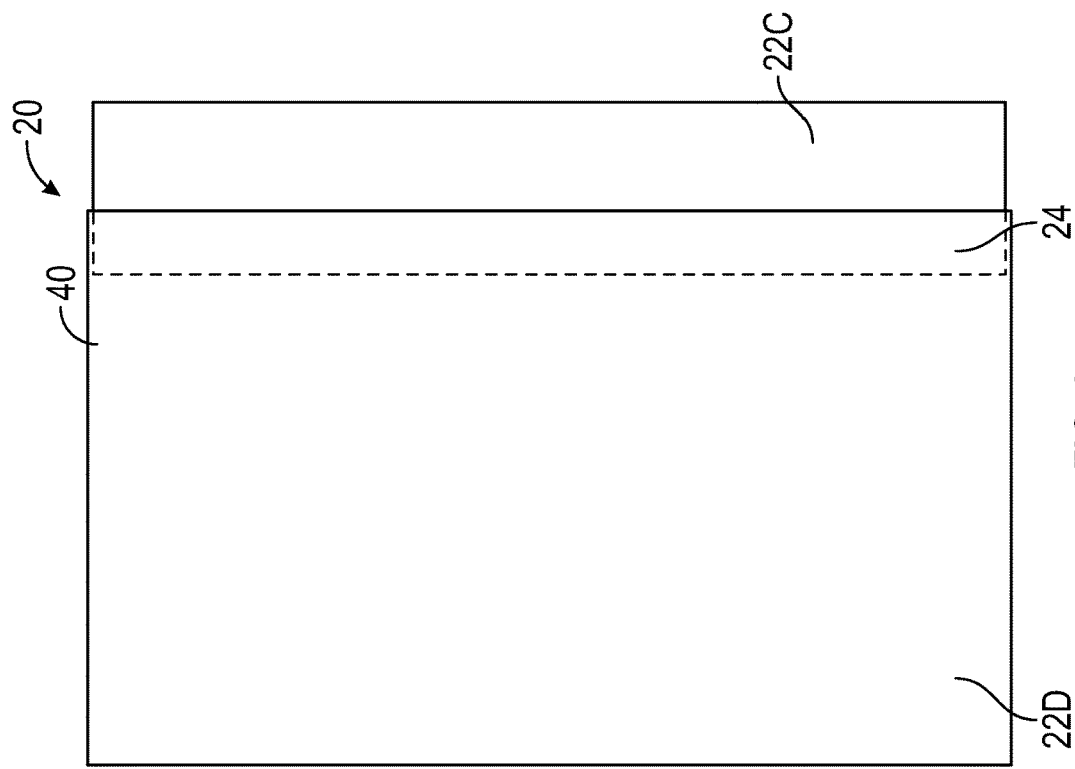
FIG. 8 is a fourth side view of the containment assembly of FIG. 4.
Figure 7:
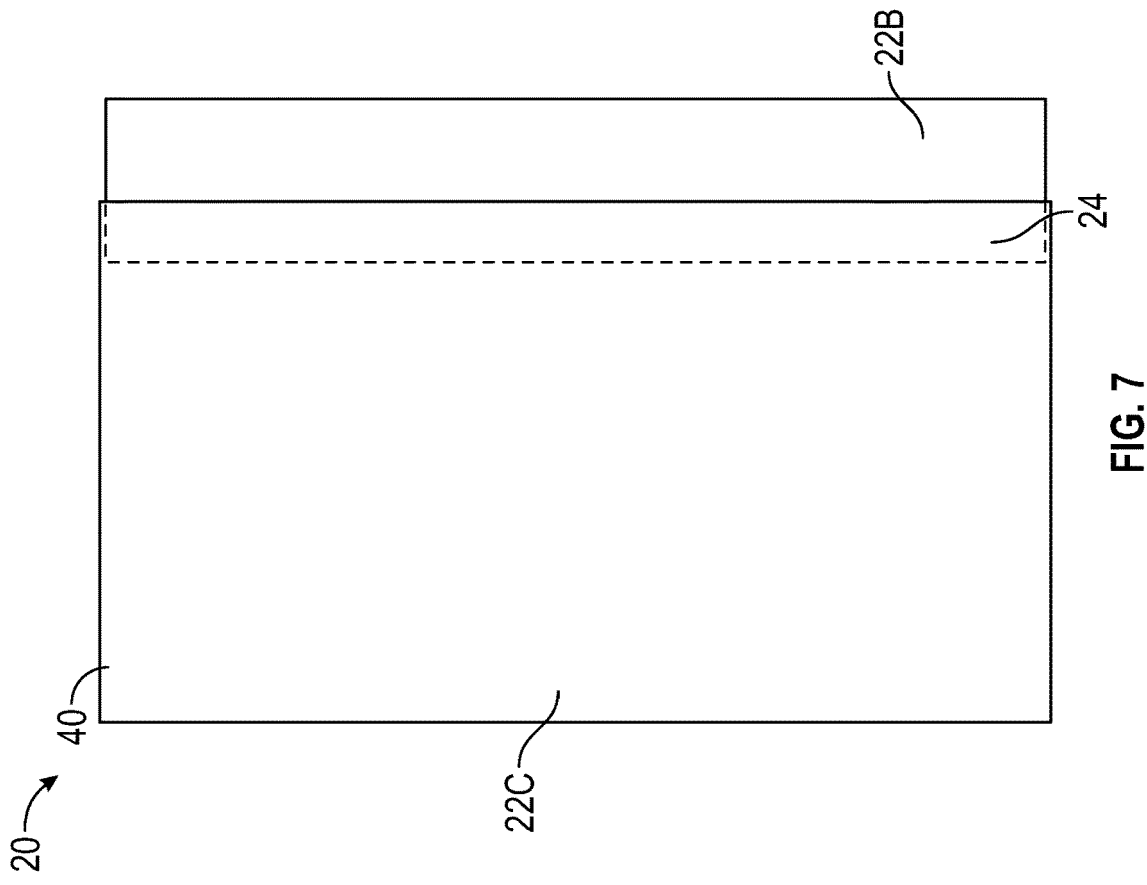
FIG. 7 is a third side view of the containment assembly of FIG. 4.
Figure 9:
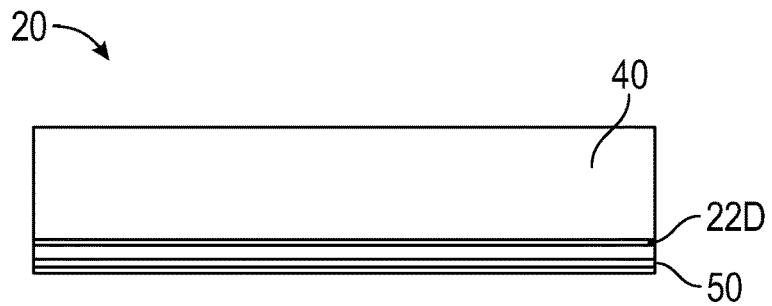
FIG. 9 is a top view of the containment curtain seal of FIG. 1.

The lateral sides or edges of panels 22 are sealingly coupled together and the upper sides or edges of panels 22 are sealingly coupled to containment cap 40 thereby forming an enclosed volume or cavity 25 within containment assembly 20 defined by panels 22. As best shown in FIG. 4, in this embodiment, the lateral sides of panels 22 overlap and are solvent welded along the overlap seams 24 to sealingly couple panels 22 together. Additionally, panels 22 sealingly engage the lateral ends 41 of containment cap 40 to seal an upper end of enclosed volume 25.

When containment assembly 20 is in the extended position shown in FIG. 2 at least partially covering wellhead 2, gaseous emissions from wellhead 2, including any VOCs, are emitted into enclosed volume 25 and are prohibited passing through panels 22 and cap 40 (i.e., prevented from exiting volume 25) into the surrounding environment without first entering detection and mitigation system 120. In particular, panels 22 and cap 40 are made of materials that prevent the passage of emitted gases thereacross. In addition, panels 22 are made of a flexible material that allows for the retraction and extension of panels 22. For instance, in this embodiment, panels 22 are made of a flexible polyvinyl fluoride (PVF) material such as the Tedlar® PVF film manufactured by the DuPont™ USA and cap 40 is made of PVC. Although enclosed volume 25 is exposed to the surrounding environment via a gap extending between the lower end 20B of the containment assembly 20 and the surface 4, in at least some applications, VOCs emitted from wellhead 2 have a density less than the surrounding air, and thus, will naturally flow upwards towards the upper end 20A of containment assembly 20, thereby preventing the VOCs from escaping into the surrounding environment through lower end 20B. In this manner, VOCs leaked from wellhead 2 are captured and contained within volume 25, and then communicated directly from volume 25 to detection and mitigation system 120.

In this embodiment, support ribs 30 of containment assembly 20 are coupled to panels 22 and are vertically spaced along the length of containment assembly 20 between upper end 20A and lower end 20B. Ribs 30 provide physical support to flexible panels 22 and add weight to panels 22 to ensure that the lower end 20B of containment assembly 20B is fully extended and positioned proximal surface 4 when containment assembly 20 is disposed in the extended position (FIG. 2). As best shown in FIGS. 1, 2, a lowermost elongate support rib 30 on each panel 22, labeled "30'" in FIGS. 1, 2, has a larger width/diameter and weight as compared to the other ribs 30 on the same panel 22 so as to provide additional weight at lower end 20B of containment assembly 20. In this embodiment, support ribs 30 are PVC pipes filled with ballast (e.g., water or sand). However, in other embodiments, the support ribs (e.g., support ribs 30) may comprise other hollow elongate members having varying shapes and formed from varying materials.

As shown particularly in FIGS. 3-11, panels 22A-22E are suspended or hung from the sides of containment cap 40, and thus, containment cap 40 physically supports panels 22A-22E at the upper end 20A of containment assembly 20. In particular, bracket assembly 60 couples containment cap 40 with panels 22A-22E and seals 50, and secures containment assembly 20 to support frame 12 at the top 15 of support frame 12. In this embodiment, containment cap 40 is a planar rectangular member including four laterally extending sides 41, a first or emissions port 42 extending therethrough, and a second or detector port 44 extending therethrough. As previously described, containment cap 40 is formed from PVC in this embodiment; however, in other embodiments, the containment cap (e.g., cap 40) may be made of other materials.

Figure 10:
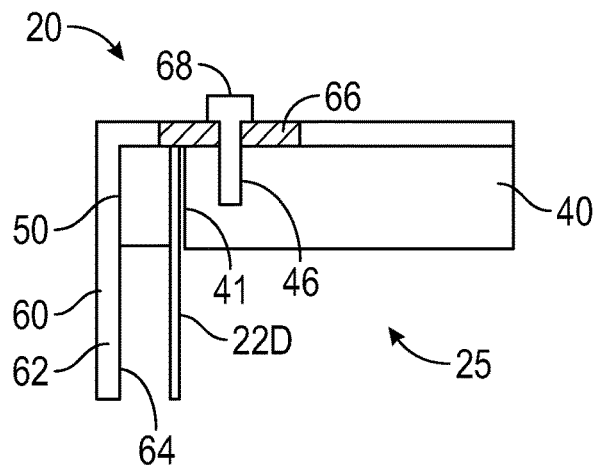
FIG. 10 is a side cross-sectional view of an embodiment of a containment bracket assembly of the containment assembly of FIG. 4 in accordance with principles disclosed herein.
Figure 11:
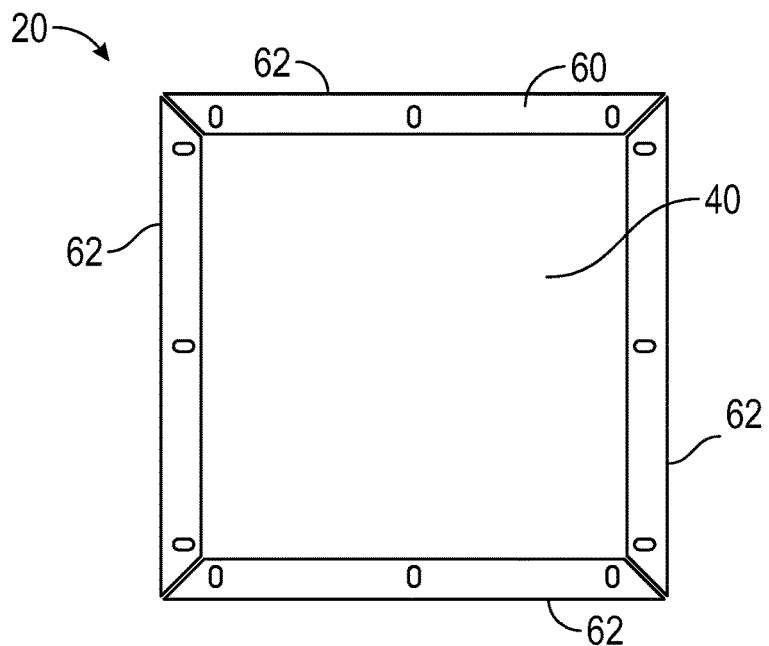
FIG. 11 is a top view of the containment bracket assembly of FIG. 10.

Containment bracket assembly 60 includes a plurality of elongate bracket members 62, each bracket member 62 having an L-shaped cross-section. Additionally, each bracket member 62 has an inner surface 64 that sealingly engages one of the elongate seals 50. As best shown in FIG. 10, panels 22A-22E (panel 22D is shown in FIG. 10) are sandwiched between seals 50 and the lateral sides 41 of containment cap 40 to secure panels 22A-22E to cap 40 while also restricting fluid communication between enclosed volume 25 and the surrounding environment. Each bracket member 62 further includes a plurality of longitudinally spaced holes or apertures 66 for receiving threaded fasteners 68 that extend through the apertures 66 of bracket members 62 and aligned apertures 46 in cap 40 proximal lateral sides 41. In this manner, bracket members 62 are releasably coupled to containment cap 40, seals 50, and panels 22A-22E to form the assembled containment assembly 20 of emissions monitoring and management system 10. In this embodiment, seals 50 each comprise elongate members having a rectangular cross-section and formed from an elastomeric material.

As shown particularly in FIGS. 1, 2, retraction mechanism 100 transitions containment assembly 20, including panels 22, between the extended and retracted positions. In this embodiment, retraction mechanism 100 is mounted to the top of containment cap 40 of containment assembly 20 and includes a flexible cable 102, a pulley 104, and a motor 106. Motor 106 is coupled to pulley 104 with a drive shaft (not shown) such that motor 106 can rotate pulley 104 in either rotational direction. Cable 102 is wound about pulley 104, passes through ribs 30 of containment assembly 20, and attaches to lowermost ribs 30' at the lower end of cable 102. In this arrangement, rotation of pulley 104 with motor 106 in a first rotational direction pays in cable 102, thereby raising panels 22 from surface 4, while rotation of pulley 104 with motor 106 in a second rotational direction opposite the first rotational direction pays out cable 102, thereby lowering panels 22 towards surface 4. In this embodiment, motor 106 is an electric motor that can be powered via a solar panel (not shown) or an electrical connection (e.g., 110 VAC) provided at the site of wellhead 2.

Detection and mitigation system 120 of the emissions monitoring and management system 10 detects the presence of predetermined gaseous emissions of interest (e.g., methane, VOCs, other reactive gases, etc.) and mitigates, reduces, or eliminates such predetermined gaseous emissions prior to being released to the surrounding environment. In this embodiment, system 120 includes a fluid conduit 122 extending from emissions port 42 of cap 40, a pump 124 coupled to conduit 122, a fluid outlet 126, a first or containment emissions detector 128 secured to containment cap 40 at port 44 of cap 40, a second or outlet emissions detector 130 mounted to outlet 126, an emissions conditioner 132 positioned between conduit 122 and outlet 126, and a transmitter 140.

In this embodiment, fluid conduit 122 of the detection and mitigation system 120 extends from emissions port 42 of containment cap 40 to emissions conditioner 132 and provides an enclosed fluid flow path between enclosed volume 25 and conditioner 132. Pump 124 selectively pumps the gases within volume 25 through conduit 122 to emissions conditioner 132. As shown particularly in FIG. 2, the one or more gases pumped from volume 25 through conduit 122 via pump 124 are denoted with arrow 17. In the event of a leak or other issue in wellhead 2, the gases within volume 25 may include one or more of the predetermined gaseous emissions of interest such as methane, VOCs, or other reactive gases. Emissions conditioner 132 is designed to reduce and/or eliminate the amount of the one or more predetermined gaseous emissions of interest (e.g., methane, VOCs, etc.) passing through conduit 122 prior to being exhausted to the surrounding environment via fluid outlet 126.

In this embodiment, containment detector 128 extends through detector port 44 of containment cap 40 into volume 25, while outlet detector 130 extends into fluid outlet 126. In this arrangement, detector 128 is in fluid communication with volume 25 (upstream of conditioner 132) and detector 130 is in fluid communication with outlet 126 (downstream of conditioner 132). Each detector 128, 130 comprises a sensor configured to detect the presence and concentration (e.g., in parts per million (PPM)) of the one or more predetermined emissions of interest, and communicate (visually and/or via a signal output) in real-time the presence and concentration of the one or more predetermined emissions of interest. In this embodiment, detectors 128, 130 communicate the detected presence and concentrations of the one or more predetermined emissions of interest in volume 25 and outlet 126, respectively, to transmitter 140 in real time via wires or cables 142 that extend between detectors 128, 130 and transmitter 140. Additionally, in this embodiment, transmitter 140 wirelessly communicates, as denoted with waveforms 144 (shown in FIG. 2) (e.g., via satellite communications), the detected presence and concentrations of the one or more predetermined emissions in volume 25 and outlet 126 in real time to a computer disposed at a location remote wellhead 2 for recordation, monitoring, and/or display (e.g., a computer at a central location for monitoring multiple wellheads 2 for leaks). With detectors 128, 130 positioned upstream and downstream, respectively, of conditioner 132, the efficiency of emissions conditioner 132 (e.g., the ability or effectiveness of conditioner 132 in removing the one or more predetermined gaseous emissions of interest) can be determined in real-time (e.g., via computer 150).

In this embodiment, during operation of emissions monitoring and management system 10, if none (or sufficiently small concentration) of the predetermined emissions of interest are detected within volume 25 by detector 128, pump 124 remains off and no gas is transported or pumped from volume 25 through conduit 122 to conditioner 132. Upon detection of one or more of the predetermined emissions of interest in volume 25 by detector 128, the concentration of the one or more predetermined emissions of interest within volume 25 can be monitored over time to determine the rate of the leak. In some applications, if the concentration of the one or more of the predetermined emissions of interest in volume 25 is sufficiently small and/or the rate of the leak is sufficiently small, the leak may be contained within volume 25 without operating pump 124 and conditioner 132. However, if the concentration of the one or more of the predetermined emissions of interest in volume 25 is sufficiently large and/or the rate of the leak is sufficiently large, pump 124 and conditioner 132 may be turned on and operated to supply gases 17 in volume 25 to conditioner 132 to reduce and/or eliminate the one or more of the predetermined emissions of interest in volume 25. The efficiency of conditioner 132 in removing the one or more of the predetermined emissions of interest in volume 25 may be monitored during its use so that remedial action can be taken (e.g., locating and fixing the leak in wellhead 2) if immediately necessary to thereby prevent an emission to the surrounding environment. Thus, the data provided by detector 128 can be utilized to selectively activate pump 124, and data provided by both detectors 128, 130 can be used to determine if and when an immediate remedial action is necessary.

In some cases, the presence and concentration of methane correlates to the presence and concentration of VOCs, and thus, by detecting the presence and concentration of methane, the presence and concentration of VOCs can be determined. In such cases, containment detector 128 comprises a sensor that detects the presence and concentration of methane in enclosed volume 25 while outlet detector 130 comprises a sensor that detects the presence and concentration of methane in fluid outlet 126.

As previously described, emissions conditioner 132 reduces and/or eliminates the presence of the one or more predetermined emissions of interest passing through fluid conduit 122 such that a reduced amount or none of the one or more predetermined emissions of interest are exposed to the surrounding environment. In general, the particular type of conditioner 132 employed in system 120 (e.g., a scrubber, catalytic converter, or a tesla converter) will depend upon the particular application and the one or more predetermined emissions of interest to be removed and/or eliminated from gases 17. For example, in embodiments where the one or more predetermined emissions of interest are VOCs, emissions conditioner 132 is a VOC scrubber configured to scrub VOCs from gases 17 flowing through conduit 122 via reacting the VOCs with a chemical or catalyst disposed in conditioner 132. In this manner, emissions conditioner 132 scrubs selected VOCs in a passive manner without needing to be provided with a stream of externally provided power or materials. This may be particularly advantageous in applications with relatively low concentrations and leak rates of the one or more predetermined emissions of interest due to the scrubber not requiring additional power for operation, which reduces the energy, and in turn, the costs of operating emissions monitoring and management system 10. In other embodiments, emissions conditioner 132 may comprise other devices configured to reduce or eliminate methane, VOCs, or other reactive gases present in gas(es) 17. For example, in some embodiments, emissions conditioner 132 is a catalytic converter that oxidizes VOCs in the presence of a catalyst. In still other embodiments, emissions conditioner 132 is a tesla converter that oxidizes VOCs at high temperatures without a catalyst. It should be appreciated that catalytic converters require additional power for heating the converter to a suitable temperature to facilitate oxidation of the VOCs in gases 17, and tesla converters require additional energy for generating an electric arc to facilitate oxidation of the VOCs in gases 17. Although in some applications catalytic converters and tesla converters may provide greater emissions reduction efficiency as compared to scrubbers, catalytic converters and tesla converters require additional energy relative to scrubbers. Accordingly, catalytic converters and tesla converters may be reserved for use in applications with relatively large concentrations and leak rates of the one or more predetermined emissions of interest. In this embodiment, emissions conditioner 132 is a passive VOC scrubber.

Figure 12:
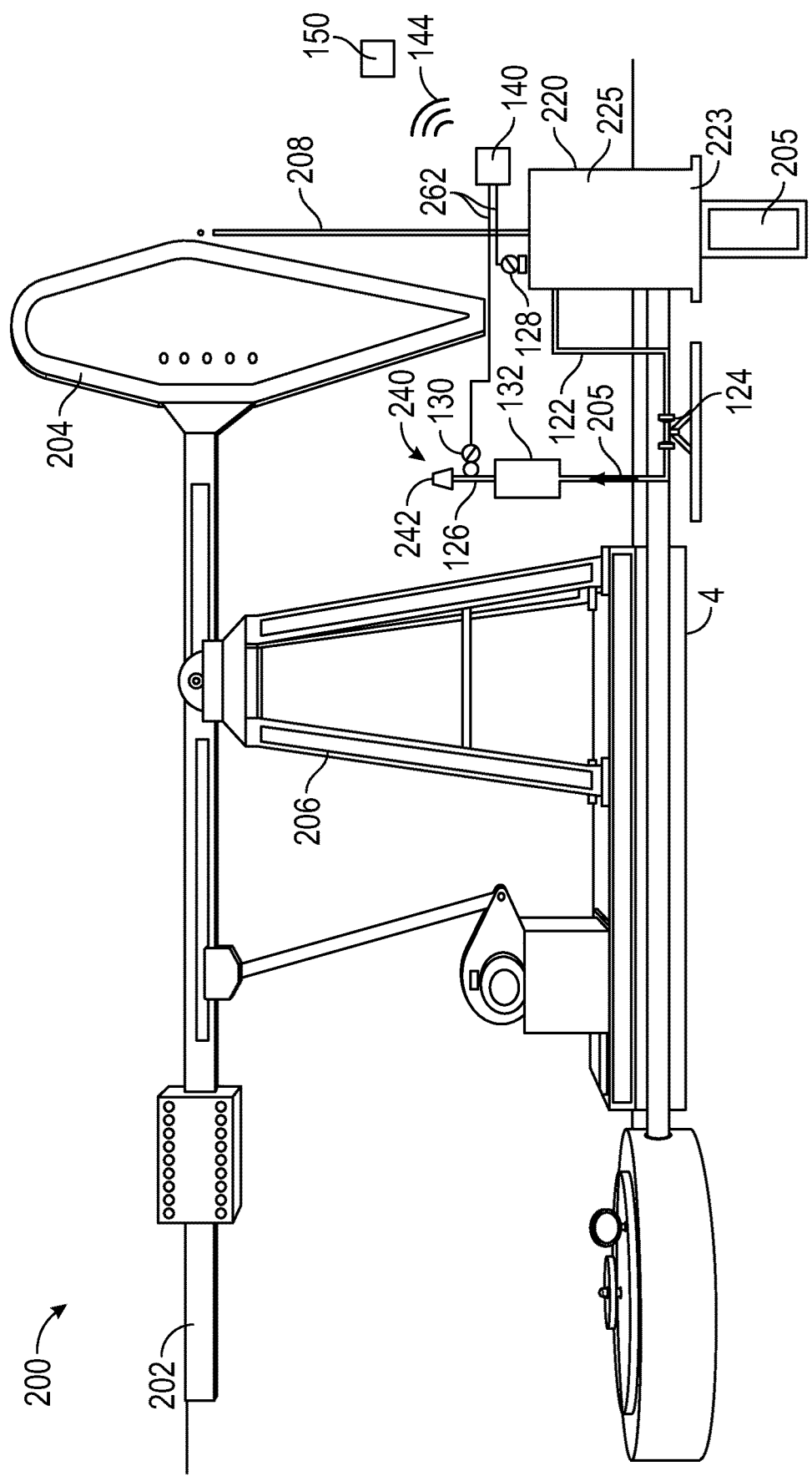
FIG. 12 is a schematic view of another embodiment of an emissions monitoring and management system in accordance with principles disclosed herein.

Referring now to FIG. 12, another embodiment of an emissions monitoring and management system 200 is shown. Similar to emissions monitoring and management system 10 described above and shown in FIGS. 1-11, emissions monitoring and management system 200 is generally configured to detect and mitigate environmentally hazardous emissions such as methane, VOCs, or other reactive compounds from an industrial component. In the embodiment of FIG. 12, emissions monitoring and management system 200 detects and mitigates environmentally hazardous emissions from a water lift system configured for displacing water from a subterranean well 205 (e.g., a gas well). Particularly, in this embodiment, emissions monitoring and management system 200 includes a water lift or pump 202, a containment vessel 220, and a detection and mitigation system 240.

Water lift 202 pumps water or other fluids from well 205 extending beneath the surface 4 proximal lift 202. In this embodiment, water lift 220 includes a pivotable beam 204, a support post 206 supporting beam 204, and a reciprocating rod 208 extending from a terminal end of beam 204. In operation, beam 204 pivots about support post 206 while rod 208 reciprocates vertically (relative the surface 4) in response to the pivoting of beam 204. Containment vessel 220 of emissions monitoring and management system 200 is disposed over the upper end of well 205 and seals targeted components of well 205 (e.g., tree, stuffing box, etc.) from the surrounding environment. Unlike the containment assembly 20 described above, containment vessel 220 is a rigid structure that physically engages and seals against well 205 to prevent fluid communication between well 205 and the surrounding environment. As will be described in more detail below, an interior sealed volume 225 of containment vessel 220 is maintained at a pressure that is below the ambient pressure of the surrounding environment to maintain a negative pressure relative to the surrounding environment, which reduces the potential for gases in vessel 220 from escaping into the surrounding environment.

Referring now to FIGS. 12-17, containment vessel 220 of emissions monitoring and management system 200 includes a plurality of planar rectangular panels 222 (labeled 222A-222F in FIGS. 13-17). In particular, panels 222 include four side panels 222A-222D extending vertically from the surface 4 and a pair of top panels 222E, 222F coupled to the upper ends of side panels 222A-222D. In addition, containment vessel 220 includes a bottom panel or base 223 (shown in FIG. 12) seated on the surface 4 and coupled to the lower ends of side panels 222A-222D to assist in containing the sealed volume 225.

As best shown in FIGS. 14-17, panels 222A-222F of containment vessel 220 are releasably coupled together via a plurality of dowel receptacles 224 that receive corresponding dowel pins 226 and a plurality of threaded apertures 228 that receive corresponding fasteners (not shown). In the embodiment of FIGS. 12-17, dowel pins 226 comprise 0.5" stainless steel rods and couple side panels 222A-222D together; however, in other embodiments, dowel pings 226 may comprise varying materials and sizes. As shown particularly in FIGS. 16 and 17, dowel pins 226 also assist in coupling together top panels 222E, 222F. Additionally, top panels 222E, 222F of containment vessel 220 each include a plurality of latches 230 for releasably coupling panels 222E, 222F together. In this embodiment, latches 230 comprise cam style 316 Stainless Steel latches; however, in other embodiments, latches 230 may comprise varying materials and configurations.

Figure 13:
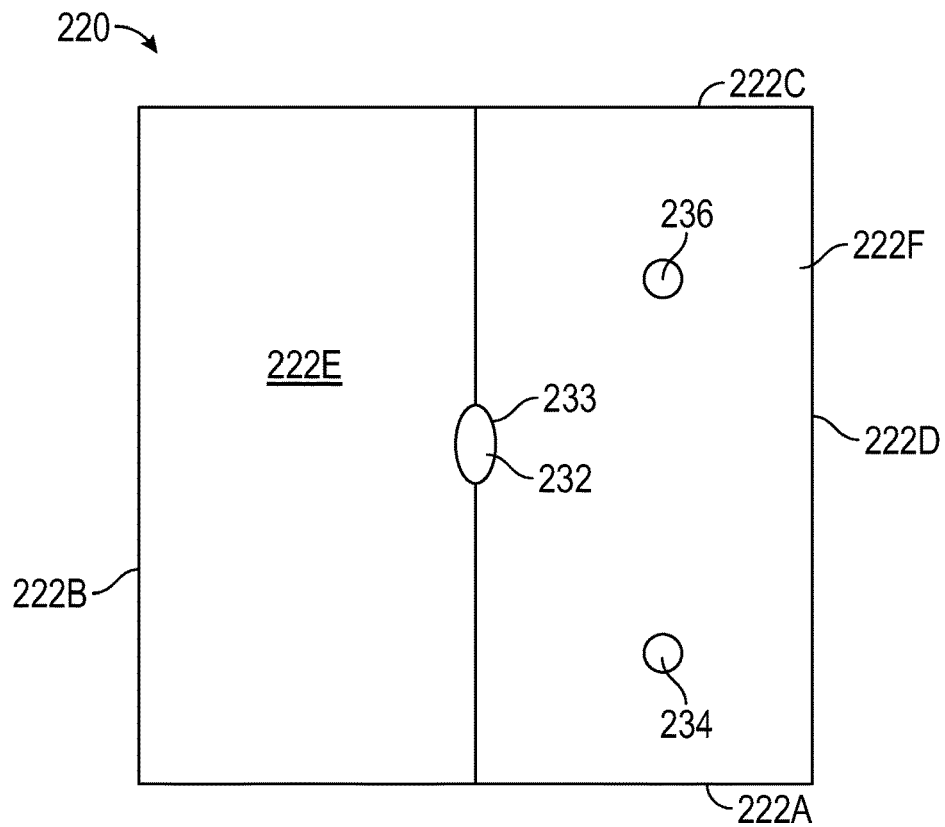
FIG. 13 is a top view of a containment vessel of FIG. 12.
Figure 14:
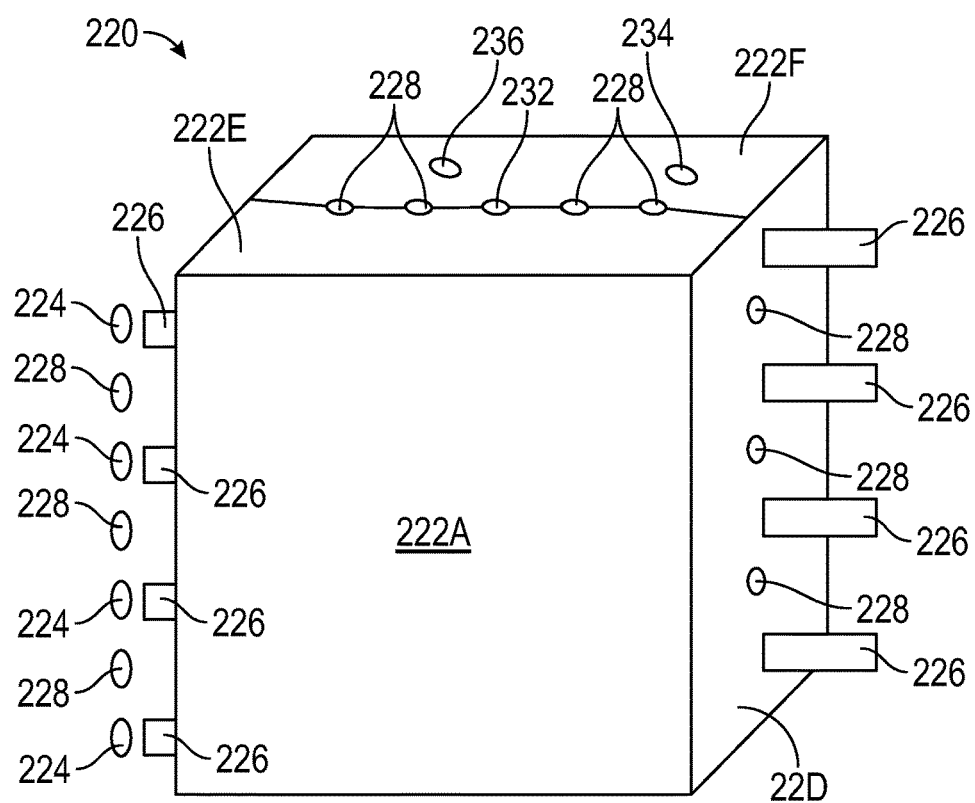
FIG. 14 is a first perspective view of the containment vessel of FIG. 13.
Figure 15:
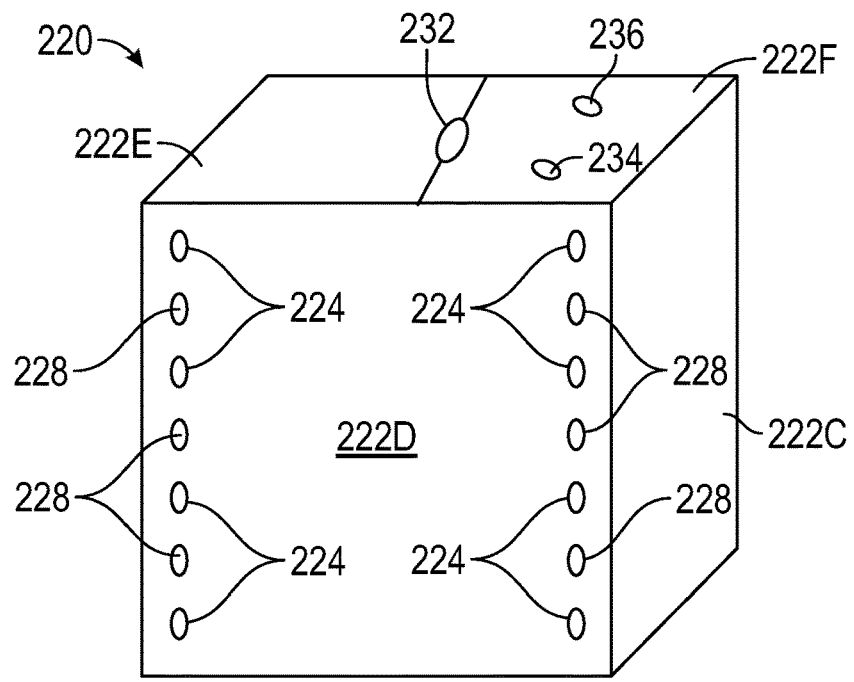
FIG. 15 is a second perspective view of the containment vessel of FIG. 13.
Figures 16, 17:
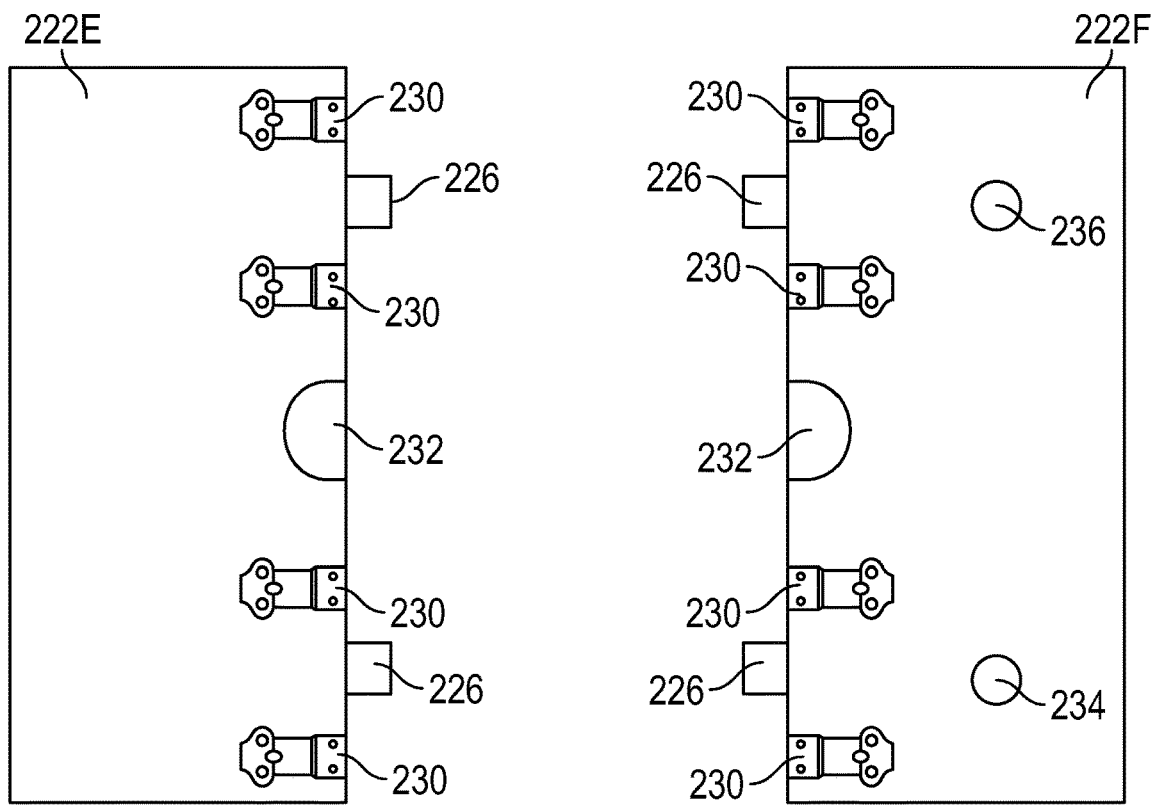
FIG. 16 is a top view of the first panel of the containment vessel of FIG. 13.
FIG. 17 is a top view of the second panel of the containment vessel of FIG. 13.

As shown particularly in FIG. 13, a rod aperture 232 is formed between top panels 222E, 222F of containment vessel 220 to allow rod 208 of pump 202 to extend into sealed volume 225 of vessel 220. Rod aperture 232 includes an annular seal 233 that sealingly engages rod 208 as rod 208 reciprocates up and down through sealed volume 225 during the operation of water lift 202 to restrict and/or prevent one or more gases within sealed volume 225 from escaping into the surrounding environment. Additionally, a first or emissions port 234 and a second or detector port 236 are also provided in top panel 222F.

As shown particularly in FIG. 12, detection and mitigation system 240 of the emissions monitoring and management system 200 functions in a similar manner as previously described. Namely, detection and mitigation system 240 detects the presence of one or more predetermined emissions of interest within the sealed volume 225 of containment vessel 220 (e.g., methane, reactive compounds such as VOCs, etc., leaked from well 205 into sealed volume 225) and mitigates, reduces, or eliminates the existence of such emissions. Detection and mitigation system 240 includes fluid conduit 122, pump 124, fluid outlet 126, emissions detectors 128, 130, conditioner 132, and transmitter 140, each as previously described. However, in this embodiment, fluid conduit 122 extends from emissions port 234 of vessel 220 and containment emissions detector 130 is secured to top panel 222F and extends through port 236 into sealed volume 225. Thus, detector 128 is in fluid communication with sealed volume 225 (upstream of conditioner 132) while detector 130 is in fluid communication with outlet 126 (downstream of conditioner 132). In addition, in this embodiment, pump 244 can be operated to flow or pump one or more gasses through conduit 122, as well as maintain a desired or predetermined negative pressure within sealed volume 225 (relative to the surrounding environment). Additionally, detection and mitigation system 240 includes a check valve 242 coupled to a terminal end of fluid outlet 126 to allow fluid flow from fluid outlet 126 to escape into the surrounding environment while restricting fluid flow from the surrounding environment into fluid outlet 126. In this manner, check valve 242 is configured to prevent air present in the surrounding environment from increasing pressure within sealed volume 225. Thus, check valve 242 is configured to assist in maintaining the negative pressure differential between the ambient pressure of the surrounding environment and pressure within sealed volume 225.

Detectors 128, 130 and transmitter 140 of detection and mitigation system 240 function as previously described with respect to detection and mitigation system 120. Particularly, detector 128, 130 comprises a sensor configured to detect the presence and concentration (e.g., in PPM) of the one or more predetermined emissions of interest, and communicate (visually and/or via a signal output) in real-time the presence and concentration of the one or more predetermined emissions of interest. In this embodiment, detectors 128, 130 communicate the detected presence and concentrations of the one or more predetermined emissions of interest in volume 225 and outlet 126, respectively, to transmitter 140 in real time via wires or cables 142. Additionally, transmitter 140 wirelessly communicates, as denoted with waveforms 144 (e.g., via satellite communications), the detected presence and concentrations of the one or more predetermined emissions in volume 225 and outlet 126 in real time to a computer 150 disposed at a location remote well 205 for recordation, monitoring, and display (e.g., a computer at a central location for monitoring multiple wells for leaks). With detectors 128, 130 positioned upstream and downstream, respectively, of conditioner 132, the efficiency of emissions conditioner 132 (i.e., the ability of conditioner 132 to remove the one or more predetermined gaseous emissions of interest) can be determined in real-time (e.g., via computer 150).

In the event of a leak at well 205, the gases within volume 225 may include one or more of the predetermined gaseous emissions of interest such as methane, VOCs, other reactive gas, etc. Emissions condition 132 reduces and/or eliminates the amount of the one or more predetermined gaseous emissions of interest (e.g., methane, VOCs, etc.) passing through conduit 122 such that a reduced amount or none of the one or more predetermined emissions of interest are exposed to the surrounding environment. Conditioner 132 of detection and mitigation system 240 may comprise a passive scrubber, a catalytic converter, or a tesla converter depending on the particular application.

In this embodiment, during operation of emissions monitoring and management system 200, if none (or sufficiently small concentration) of the predetermined emissions of interest are detected within volume 225 by detector 128, pump 124 may remain off (e.g., no gas is transported or pumped from volume 225 through conduit 122 to conditioner 132) or operated solely to maintain the negative pressure within volume 225. Upon detection of one or more of the predetermined emissions of interest in volume 225 by detector 128, the concentration of the one or more predetermined emissions of interest within volume 225 is monitored over time to determine the rate of the leak. In some applications, if the concentration of the one or more of the predetermined emissions of interest in volume 225 is sufficiently small and/or the rate of the leak is sufficiently small, the leak may be contained within volume 225 without operating pump 124 and conditioner 132, or by operating pump 124 at a relatively slow pumping rate to maintain the negative pressure within sealed volume 225. However, if the concentration of the one or more of the predetermined emissions of interest in volume 225 is sufficiently large and/or the rate of the leak is sufficiently large, pump 124 may be turned on or operated at a faster rate to supply one or more gases in sealed volume 225 to conditioner 132 to reduce and/or eliminate the one or more of the predetermined emissions of interest in sealed volume 225. The efficiency of conditioner 132 in removing the one or more of the predetermined emissions of interest in sealed volume 225 is preferably monitored during its use so that remedial action can be taken (e.g., locating and fixing the leak in well 205) if immediately necessary to thereby prevent an emission to the surrounding environment. Thus, the data provided by detector 128 can be utilized to selectively activate pump 124, and data provided by both detectors 128, 130 can be used to determine if and when an immediate remedial action is necessary.

In embodiments where conditioner 132 requires power to operate (e.g., conditioner 132 is a catalytic converter or tesla converter), pump 124 may be operated to maintain the negative pressure within volume 225 without supplying power to conditioner 132 (i.e., without conditioner 132 turned on) when none (or sufficiently small concentration) of the predetermined emissions of interest are detected within volume 225 by detector 128. However, in this embodiment, once a sufficiently large concentration of the predetermined emissions of interest are detected within volume 225 by detector 128, converter 132 may be turned on. In this manner, converter 132 is only operated when a sufficiently large concentration of the predetermined emissions of interest are detected by detector 128 despite pump 124 being continuously monitored to maintain a negative pressure within volume 225, thereby minimizing the energy demands of detection and mitigation system 240.

Figure 18:
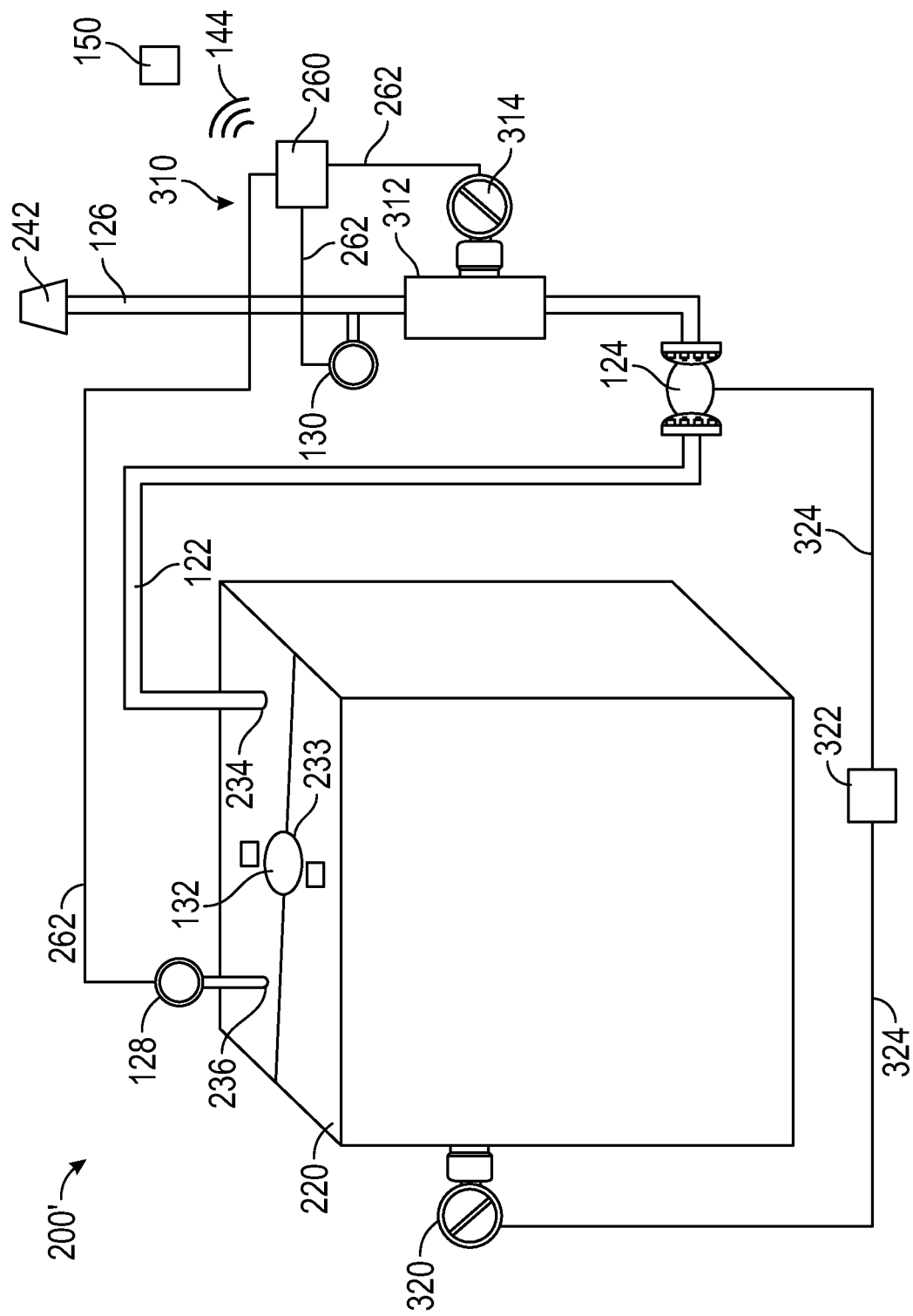
FIG. 18 is a schematic view of another embodiment of an emissions monitoring and management system in accordance with principles disclosed herein.

As previously described, in some embodiments, the emissions conditioner (e.g., conditioner 132) can be catalytic converters or a tesla converters. Referring briefly to FIG. 18, another embodiment of an emissions monitoring and management system 200' including a detection and mitigation system 310 employing a catalytic converter 312 instead of a passive VOC scrubber is shown. In the embodiment of FIG. 18, catalytic converter 312 detection and mitigation system 310 is disposed at the outlet of conduit 122 between pump 124 and fluid outlet 126. As previously described, catalytic converters 312 typically require a heater that is used in conjunction with a catalyst to reduce and/or eliminate one or more predetermined emissions of interest. Thus, in this embodiment, catalytic converter 312 includes a switch or sensor 314. Switch 314 is electrically coupled to transmitter 140 via a cable 262 extending therebetween such that transmitter 140 can communicate a control signal to switch 314 for its activation and communicate the status of switch 314 to computer 150. In this embodiment, switch 314 comprises a temperature switch configured to sense or monitor the temperature of catalytic converter 312. In this embodiment, in response to measuring a first predetermined concentration of a predetermined gas of interest (e.g., VOCs, etc.), converter 312 is turned on to begin pre-heating converter 312 for operation. Once converter 312 reaches a sufficient or threshold operating temperature, the detection and mitigation system 310 is activated and one or more predetermined gases of interest within containment vessel 220 are actively managed. In other embodiments, switch 314 comprises a flow switch or sensor 314 configured to actively measure a fluid flow rate of gases flowing through detection and mitigation system 310 (e.g., through converter 312, etc.), where the fluid flow rate data of system 310 may be transmitted in real-time via transmitter 140.

In this embodiment, containment vessel 220 includes a pressure differential switch or sensor 320 in signal communication with a controller 322 via a signal pathway or cable 324 extending therebetween. Controller 322 is also in signal communication with pump 124 via a signal pathway or cable 324 extending therebetween for controlling the actuation of pump 124 in response to a signal output provided by differential pressure switch 320. In particular, differential pressure switch 320 is configured to measure the differential pressure between sealed volume 225 of containment vessel 220 and the surrounding environment, and communicate the measured pressure differential to controller 322, which operates pump 124 in response to the measured pressure differential to maintain a desired or predetermined pressure differential between sealed volume 225 and the surrounding environment. In some embodiments, controller 322 may be placed in signal communication with transmitter 260 for transmitting differential pressure measurements of switch 320 to computer 150.

In general, computer 150 is configured to process data communicated to computer 150 from respective detection and mitigation systems (e.g., detection and mitigation systems 120, 310) to identify and monitor the leakage of one or predetermined emissions of interest. In some embodiments, computer 150 monitors and reports one or more of the following: (1) the presence of one or more predetermined emissions of interest (e.g., methane, VOCs, or other reactive gases) inside a containment volume (e.g., within sealed volumes 25, 225); (2) the concentration of the one or more predetermined emissions of interest inside the containment volume; (3) the concentration of the one or more predetermined emissions of interest at a fluid outlet (e.g., fluid outlet 126) downstream of an emissions conditioner (e.g., emissions conditioners 132, 312); (4) the efficiency of the emissions conditioner (i.e., measure of the ability of the emissions conditioner to reduce and/or eliminate the one or more predetermined emissions of interest); (5) the change in the concentration of the one or more predetermined emissions of interest in the containment volume over time as a measure or indicator of the volumetric leak rate of the one or more predetermined emissions of interest from the source (e.g., an average change in the concentration of the one or more predetermined emissions of interest in the containment volume over a known period of time such as one hour, 24 hours, one month, quarterly, etc.); and (6) the differential pressure between the containment volume and the environment surrounding the containment volume. In some embodiments, the emissions report provided by computer 150 may be provided to an applicable regulatory agency to confirm compliance with applicable rules or regulations.

In some embodiments, computer 150 transmits signals or commands to transmitter 140 for controlling the operation of the respective emissions monitoring and management system (e.g., systems 100, 200, and 200'). For instance, in some embodiments, computer 150 provides a control signal to the transmitter 140 for controlling the operation of the pump (e.g., pump 124) and/or the emissions conditioner (e.g., conditioners 132, 312). In embodiments where the emissions conditioner is a converter (e.g., conditioner 312), such as the catalytic and tesla converters described above, computer 150 is transmit a control signal to the transmitter to energize or heat the converter in response to the measurement of a first threshold concentration of the one or more predetermined emissions of interest within the containment volume (e.g., volume 25, 225). In such embodiments, computer 150 may also be configured to actuate the pump to flow gases from the containment volume to the emissions conditioner in response to the measurement of a second threshold concentration of the one or more predetermined emissions of interest within the containment volume that is greater than the first threshold concentration. This functionality advantageously allows the converter to sufficiently heat before the concentration of the one or more predetermined emissions of interest within the containment volume reach the second threshold level. Moreover, as described above, computer 150 can also provide a control signal to the transmitter to actuate the pump to reduce a pressure within the containment volume in response to a measurement provided by a differential pressure switch (e.g., differential pressure switch 320).

In the manner described, the emissions monitoring and management systems 10, 200, 200' described above provide real-time emissions monitoring and mitigation or elimination. In particular, systems 10, 200, 200' provide active monitoring and mitigation functionality to reduce and/or eliminate the leakage of one or more predetermined emission of interest into the surrounding environment at a remote location. Additionally, the active monitoring functionality provided by systems 10, 200, 200' also provides the advantage of allowing an operator of the system to proactively maintain and/or repair industrial equipment in the field in response to the detection of an emission, providing for additional flexibility and minimizing any downtime or delays in the operation of said equipment.

While embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. An emissions monitoring and management system, comprising:
   a containment assembly that defines an enclosed volume, wherein the enclosed volume of the containment assembly is configured to receive an industrial component comprising a wellhead;
   a fluid conduit coupled to the containment assembly and in fluid communication with the enclosed volume;
   an emissions conditioner coupled to the fluid conduit, wherein the emissions conditioner is configured to reduce a concentration of a predetermined gas of interest in the fluid conduit;
   a first emissions detector coupled to the containment assembly and in fluid communication with the enclosed volume, wherein the first emissions detector is configured to determine a concentration of the predetermined gas of interest in the enclosed volume; and
   a transmitter in signal communication with the first emissions detector, wherein the transmitter is configured to transmit signals corresponding to a first predetermined concentration of the predetermined gas of interest in the enclosed volume.

2. The system of claim 1, further comprising a computer in wireless communication with the transmitter, wherein the computer is configured to output an emissions report including the concentration of the predetermined gas of interest in the enclosed volume.

3. The system of claim 2, further comprising:
   a second emissions detector coupled to a fluid outlet extending from the emissions conditioner, wherein the second emissions detector is in fluid communication with a surrounding environment, and wherein the second emissions detector is configured to determine a concentration of the predetermined gas of interest in the fluid outlet;
   wherein the computer is in signal communication with the first and second emissions detectors and is configured to determine an efficiency of the emissions conditioner based on the difference between concentration of the predetermined gas of interest in the enclosed volume determined by the first emissions detector and the concentration of the predetermined gas of interest in the fluid outlet determined by the second emissions detector.

4. The system of claim 1, further comprising a pump coupled to the fluid conduit and configured to pump the predetermined gas of interest from the enclosed volume through the fluid conduit to the emissions conditioner.

5. The system of claim 1, wherein the emissions conditioner comprises a scrubber, a catalytic converter, or a tesla converter.

6. The system of claim 1, wherein the emissions conditioner is a catalytic converter comprising a temperature switch configured to monitor a temperature of the catalytic converter, and wherein the transmitter is in signal communication with the temperature switch.

7. The system of claim 1, wherein the transmitter is configured to transmit signals corresponding to a second predetermined concentration of the predetermined gas of interest in the enclosed volume, wherein the second predetermined concentration is greater than the first predetermined concentration.

8. The system of claim 1, wherein the containment assembly comprises a plurality of flexible panels suspended from a frame, and wherein the enclosed volume is in fluid communication with the surrounding environment.

9. The system of claim 1, wherein the containment assembly comprises a containment vessel sealed from the surrounding environment.

10. The system of claim 9, further comprising:
a pressure differential switch coupled to the containment vessel; and
a controller in communication with the pressure differential switch, wherein the controller is configured to actuate a pump to maintain a negative pressure in the enclosed volume relative to the surrounding environment.

11. The system of claim 1, further comprising a flow switch configured to measure a fluid flow rate in the emissions conditioner, wherein the flow switch is in signal communication with the transmitter.

12. An emissions monitoring and management system, comprising:
a containment assembly that defines an enclosed volume, wherein the enclosed volume of the containment assembly is configured to receive an industrial component, the containment assembly has a first end, a second end opposite the first end, the containment assembly comprising:
a plurality of flexible panels extending between the first end and the second end, the panels defining the enclosed volume;
wherein the containment assembly comprises a retracted position spaced from the industrial component and an extended position at least partially covering the industrial component when the containment assembly is located over the industrial component;
a fluid conduit coupled to the containment assembly and in fluid communication with the enclosed volume;
an emissions conditioner coupled to the fluid conduit, wherein the emissions conditioner is configured to reduce a concentration of a predetermined gas of interest in the fluid conduit;
a first emissions detector coupled to the containment assembly and in fluid communication with the enclosed volume, wherein the first emissions detector is configured to detect the presence of the predetermined gas of interest in the enclosed volume; and
a retraction mechanism coupled to the containment assembly and configured to selectively actuate the containment assembly between the retracted position and the extended position.

13. The system of claim 12, further comprising:
a support frame that physically supports the containment assembly, the support frame comprising:
a plurality of laterally spaced legs defining lateral sides of the support frame;
a support beam extending between a pair of the plurality of laterally spaced legs that defines a top of the support frame;
wherein the containment assembly further comprises:
a containment cap attached to a first end of each flexible panel via a bracket assembly, the containment cap comprising a detector port that receives the first emissions detector;
a plurality of elongate containment seals that sealingly engage the flexible panels and the bracket assembly to restrict fluid disposed in the enclosed volume from escaping into the surrounding environment at the first end of the containment assembly.

14. The system of claim 13, wherein:
each of the plurality of legs of the support frame comprises a tubular member including an internal cavity configured to receive ballast; and
at least one of the plurality of legs of the support frame includes a fill aperture at a first end of the leg and a drain aperture at a second end of the leg opposite the first end, and wherein both the fill aperture and the drain aperture are configured to allow for the selective passage of ballast therethrough.

15. The system of claim 14, wherein the containment assembly further comprises:
a plurality of elongate ribs extending laterally along the flexible panels;
wherein each of the plurality of elongate ribs, legs, and beams comprise a plastic material.

16. The system of claim 12, further comprising:
a second emissions detector coupled to a fluid outlet extending from the emissions conditioner, wherein the second emissions detector is in fluid communication with a surrounding environment, and wherein the second emissions detector is configured to determine a concentration of the predetermined gas of interest in the fluid outlet;
a transmitter in signal communication with the first and second emissions detectors; and
a computer in signal communication with the first and second emissions detectors;
wherein the first emissions detector is configured to determine a concentration of the predetermined gas of interest in the enclosed volume;
wherein the transmitter is configured to transmit signals corresponding to a first predetermined concentration of the predetermined gas of interest in the enclosed volume; and
wherein the computer is configured to measure an efficiency of the emissions conditioner based on the difference between concentration of the predetermined gas of interest in the enclosed volume determined by the first emissions detector and the concentration of the predetermined gas of interest in the fluid conduit determined by the second emissions detector.

17. A method for monitoring and managing emissions from an industrial component, comprising:
(a) at least partially covering the industrial component with a containment assembly that defines an enclosed volume;
(b) determining a concentration of a predetermined gas of interest in the enclosed volume;
(c) communicating one or more gases from the enclosed volume through a fluid conduit to an emissions conditioner to reduce a concentration of the predetermined gas of interest in the fluid conduit;
(d) determining a concentration of the predetermined gas of interest in a fluid outlet extending from the emissions conditioner; and (e) transmitting signals corresponding to a first predetermined concentration of the predetermined gas of interest in the enclosed volume.

18. The method of claim 17, further comprising:
(f) actuating the containment assembly between a retracted position spaced from the industrial component and an extended position at least partially covering the industrial component.

19. The method of claim 17, further comprising:
(f) determining an efficiency of the emissions conditioner based on the difference between concentration of the predetermined gas of interest in the enclosed volume and the concentration of the predetermined gas of interest in the fluid outlet.

* * * * *